United States Patent [19]

Ubasawa et al.

[11] Patent Number: 5,206,255
[45] Date of Patent: Apr. 27, 1993

[54] HETEROCYCLIC COMPOUND

[75] Inventors: Masaru Ubasawa; Shuitiro Kadowaki, both of Yokohama; Yoshio Hayashi, Ushiku, all of Japan

[73] Assignee: Mitsubishi Kasei Corporation, Tokyo, Japan

[21] Appl. No.: 588,549

[22] Filed: Sep. 26, 1990

[30] Foreign Application Priority Data

Sep. 29, 1989 [JP] Japan .................. 1-254530

[51] Int. Cl.$^5$ .................... C02D 263/32; A61K 31/42
[52] U.S. Cl. .................... 514/374; 514/375; 548/179; 548/203; 548/217; 548/235
[58] Field of Search .................... 548/203, 235, 217; 514/374, 375

[56] References Cited

U.S. PATENT DOCUMENTS

| | | | |
|---|---|---|---|
| 3,574,218 | 4/1971 | Hideg et al. | 260/293.4 |
| 4,168,379 | 9/1979 | Boell | 546/112 |
| 4,594,425 | 6/1986 | Musser et al. | 548/235 |
| 4,675,405 | 6/1987 | Musser et al. | 546/172 |
| 4,732,978 | 3/1988 | Kreft et al. | 546/152 |
| 4,772,703 | 9/1988 | Musser et al. | 544/283 |
| 4,904,786 | 2/1990 | Musser et al. | 546/152 |

FOREIGN PATENT DOCUMENTS

| | | |
|---|---|---|
| 1038393 | 9/1978 | Canada . |
| 0015005 | 9/1980 | European Pat. Off. . |
| 219436 | 4/1987 | European Pat. Off. . |
| 0283035 | 9/1988 | European Pat. Off. . |
| 318084 | 5/1989 | European Pat. Off. . |
| 318085 | 5/1989 | European Pat. Off. . |
| 351194 | 1/1990 | European Pat. Off. ............ 548/203 |

OTHER PUBLICATIONS

Noyanalpan Gazi Univ. Eczacilik Fak Derg 1986 3(1) 1-11.
Vol. 69, 1968: 43837v.
Vol. 78, 1973: 147860z.
Vol. 104, 1986: 218613q.
Vol. 104, 1986: 161786s.
Vol. 105, 1986: 126825c.
Vol. 108, 1988: 19057u.

Primary Examiner—Robert Gerstl
Attorney, Agent, or Firm—Oblon, Spivak, McClelland, Maier & Neustadt

[57] ABSTRACT

A novel heterocyclic compound represented by the following formula (I):

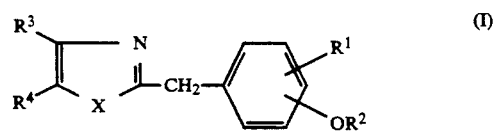

wherein X represents an oxygen atom or sulfur atom; $R^1$ represents a hydrogen atom or halogen atom; $R^2$ represents a $C_4$-$C_6$ alkyl group, $C_2$-$C_{10}$ alkoxyalkyl group, $C_3$-$C_{15}$ alkenyl group, $C_7$-$C_{12}$ aralkyl group, $C_8$-$C_{18}$ aralkyloxyalkyl group, $C_7$-$C_{12}$ aryloxyalkyl group, $C_3$-$C_{10}$ alkynyl group, $C_4$-$C_{12}$ alkadienyl group, $C_6$-$C_{18}$ alkatrienyl group, $C_6$-$C_{12}$ alkadiynyl group, or $C_6$-$C_{12}$ alkatriynyl group, said aryloxyalkyl group, alkynyl group, alkadienyl group, alkatrienyl group, alkadiynyl group and alkatriynyl group being capable of having at least one substituent selected from the group consisting of halogen atoms, $C_1$-$C_4$ alkyl group, $C_1$-$C_4$ halogenated alkyl group, phenyl group, hydroxyl group and $C_1$-$C_4$ alkoxy group; and each of $R^3$ and $R^4$ independently represents a hydrogen atom, $C_1$-$C_6$ alkyl group, phenyl group or tolyl group, or $R^3$ and $R^4$ may be combined together to from a benzene ring which may have at least one halogen atom; or a pharmaceutically acceptable salt thereof. The compound according to the present invention has an effect of inhibiting lipoxygenase and suppresses the formation of leukotrienes and, accordingly, useful for the prevention and treatment of inflammation, rheumatism and various allergic diseases.

9 Claims, No Drawings

HETEROCYCLIC COMPOUND

BACKGROUND OF THE INVENTION

The present invention relates to a novel heterocyclic compound having an inhibition activity to lipoxygenase and useful as an anti-inflammatory agent or anti allergic agent.

In mammal animals, autacoid such as prostaglandins, thromboxanes, prostacyclin and leukotrienes playing an important role for the physiological state and manifestation of disease are formed from arachidonic acid, $C_{20}$ unsaturated fatty acid, by way of several biological enzymatic reactions. For instance, prostaglandins or thromboxanes are formed by the action of cyclooxygenase and leukotrienes are formed by the action of lipoxygenase. Among them, it has been know that leukotriene $B_4$, $C_4$ and $D_4$, for instance, is greatly concerned in inflammation or allergic reaction.

For instance, leukotriene $B_4$ has a strong chemotactic effect to leucocyte (A. W. Ford-Hutchinson, J. Roy. Soc. Med., 74, 831-833 (1981)), and leukotriene $C_4$ or leukotriene $D_4$ is concerned in inflammatory reaction as a vascular permeability factor, as well as exhibits strong bronchoconstriction effect on human bronchi (Dahlen et al., Nature, 288, 484-486 (1980)).

In has, accordingly, been considered that inflammation, rheumatism, allergic disease (allergic bronchial asthma, allergic rhinitis, allergic dermatitis and other allergic hypersensitivities) etc. can be prevented or cured by inhibiting lipoxygenase thereby suppressing the formation of leukotrienes. The use of compounds having an inhibition activity to lipoxygenase as anti-inflammatory agent or anti allergic agent has been described, for example, in Japanese Patent Application Laid-Open (KOKAI) No.62-142167 and No.62-190159, etc.

On the other hand, it has also been reported that benoxaprofen having an inhibition activity to lipoxygenase is effective to psoriasis which is an intractable cutaneous disease, but it has a grave adverse effect (Archives of Dermatology, 119, 548 (1983); British Medical Journal (Br. Med. J.) 282, 1433 (1981)).

In view of the above, it has been demanded for the development of a novel compound inhibiting lipoxygenase more effectively.

SUMMARY OF THE INVENTION

In view of the above, the present inventors have noted on thiazole, oxazole, benzothiazole and benzoxazole derivatives and have made an extensive study for providing a compound which has an inhibition activity to lipoxygenase and is effective as anti-inflammatory agent or anti allergic agent and, as a result, have found that the intended purpose can be attained by a compound represented by the formula (I) shown below. The present invention has been accomplished based on this finding.

DETAILED DESCRIPTION OF THE INVENTION

The novel heterocyclic compound of the present invention is represented by the following general formula (I):

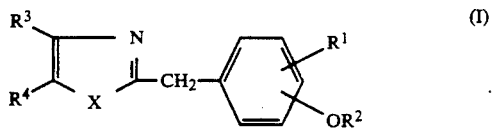

or a pharmaceutically acceptable salt thereof.

In the above formula (I), X represents an oxygen atom or sulfur atom, preferably an oxygen atom.

$R^1$ represents a hydrogen atom or halogen atom such as chlorine atom, fluorine atom and bromine atom, preferably, a hydrogen atom or chlorine atom.

$R^2$ represents a $C_4$–$C_6$ alkyl group, $C_2$–$C_{10}$ alkoxyalkyl group, $C_3$–$C_{15}$ alkenyl group, $C_7$–$C_{12}$ aralkyl group, $C_8$–$C_{18}$ aralkyloxyalkyl group, $C_7$–$C_{12}$ aryloxyalkyl group, $C_3$–$C_{10}$ alkynyl group, $C_4$–$C_{12}$ alkadienyl group, $C_6$–$C_{18}$ alkatrienyl group, $C_6$–$C_{12}$ alkadiynyl group, or $C_6$–$C_{12}$ alkatriynyl group. The aryloxyalkyl group, alkynyl group, alkadienyl group, alkatrienyl group, alkadiynyl group and alkatriynyl group may have at least one substituent selected from the group consisting of halogen atoms, $C_1$–$C_4$ alkyl group, $C_1$–$C_4$ halogenated alkyl group, phenyl group, hydroxyl group and $C_1$–$C_4$ alkoxy group.

Preferably, $R^2$ is a $C_4$–$C_6$ alkyl group, $C_2$–$C_6$ alkoxyalkyl group, $C_3$–$C_{10}$ alkenyl group, $C_7$–$C_{12}$ aralkyl group, $C_8$–$C_{12}$ aralkyloxyalkyl group, $C_7$–$C_{12}$ aryloxyalkyl group which may have at least one substituent selected from the group consisting of halogen atoms, $C_1$–$C_4$ alkyl group and $C_1$–$C_4$ halogenated alkyl group, $C_3$–$C_{10}$ alkynyl group which may have at least one substituent selected from the group consisting of phenyl group, hydroxyl group and $C_1$–$C_4$ alkoxy group, $C_5$–$C_{12}$ alkadienyl group, $C_7$–$C_{18}$ alkatrienyl group, or $C_6$–$C_{12}$ alkadiynyl group which may have at least one substituent selected from the group consisting of phenyl group, hydroxyl group and $C_1$–$C_4$ alkoxy group.

More preferably, $R^2$ is a $C_4$–$C_6$ alkyl group, $C_2$–$C_6$ alkoxyalkyl group, $C_3$–$C_{10}$ alkenyl group, $C_7$–$C_{10}$ aralkyl group, $C_8$–$C_{10}$ aralkyloxyalkyl group, $C_9$–$C_{12}$ aryloxyalkyl group which may have at least one substituent selected from the group consisting of chlorine atom, fluorine atom, $C_1$–$C_4$ alkyl group and trifluoromethyl group, $C_3$–$C_8$ alkynyl group which may have at least one substituent selected from the group consisting of phenyl group, hydroxyl group and $C_1$–$C_4$ alkoxy group, $C_5$–$C_{10}$ alkadienyl group, $C_7$–$C_{15}$ alkatrienyl group, or $C_8$–$C_{11}$ alkadiynyl group which may have at least one substituent selected from the group consisting of phenyl group, hydroxyl group and $C_1$–$C_4$ alkoxy group.

Further preferably, $R^2$ is a $C_4$–$C_6$ alkyl group, $C_2$–$C_6$ alkoxyalkyl group, $C_8$–$C_{10}$ aralkyloxyalkyl group, $C_9$–$C_{12}$ aryloxyalkyl group which may have at least one substituent selected from the group consisting of chlorine atom, fluorine atom, $C_1$–$C_4$ alkyl group and trifluoromethyl group, $C_3$–$C_8$ alkynyl group which may have at least one substituent selected from the group consisting of phenyl group, hydroxyl group and $C_1$–$C_4$ alkoxy group, or $C_8$–$C_{11}$ alkadiynyl group which may have at least one substituent selected from the group consisting of phenyl group, hydroxyl group and $C_1$–$C_4$ alkoxy group.

Each of $R^3$ and $R^4$ independently represents a hydrogen atom, $C_1$–$C_6$ alkyl group, phenyl group or tolyl group, preferably a hydrogen atom or phenyl group. Further, $R^3$ and $R^4$ may be combined together to form a benzene ring which may have at least one halogen atom such as chlorine atom, bromine atom and fluorine atom, preferably chlorine atom.

As the examples of the compounds of the present invention described above, there can be mentioned those as shown in the following Table 1.

TABLE 1

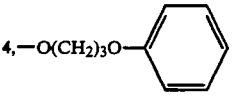

| Compound No. | X | R$^1$ | OR$^2$ | R$^3$ | R$^4$ |
| --- | --- | --- | --- | --- | --- |
| 1 | S | H | 4,—O(CH$_2$)$_3$O— | | 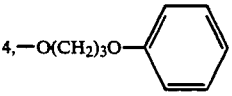 |
| 2 | O | H | 4,—O(CH$_2$)$_3$O— | | 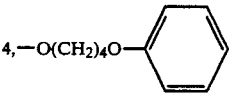 |
| 3 | O | H | 4,—O(CH$_2$)$_4$O— | | 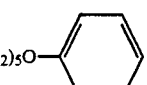 |
| 4 | O | H | 4,—O(CH$_2$)$_5$O— | | 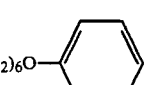 |
| 5 | O | H | 4,—O(CH$_2$)$_6$O— | | 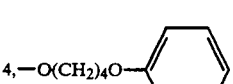 |
| 6 | O | 2,—Cl | 4,—O(CH$_2$)$_4$O— | | 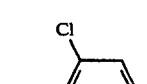 |
| 7 | O | H | 4,—O(CH$_2$)$_4$O— (Cl) | | 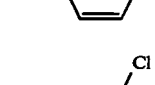 |
| 8 | O | H | 4,—O(CH$_2$)$_4$O— (Cl) | | 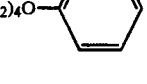 |
| 9 | O | H | 4,—O(CH$_2$)$_4$O——Cl | | 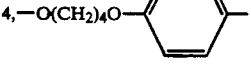 |
| 10 | O | H | 4,—O(CH$_2$)$_4$O— (CH$_3$) | | |

TABLE 1-continued

[Structure: R³ and R⁴ on a ring connected via C=N-CH₂ to a benzene ring (positions 1-6) bearing R¹ at position 3 and OR² at position 4, with X between R and the C=N carbon]

| Compound No. | X | R¹ | OR² | R³ | R⁴ |
|---|---|---|---|---|---|
| 11 | O | H | 4,—O(CH₂)₄O—(3-CH₃-phenyl) | benzene | |
| 12 | O | H | 4,—O(CH₂)₄O—(4-CH₃-phenyl) | benzene | |
| 13 | O | H | 4,—O(CH₂)₄O—(2-F-phenyl) | benzene | |
| 14 | O | H | 4,—O(CH₂)₄O—(3-F-phenyl) | benzene | |
| 15 | O | H | 4,—O(CH₂)₄O—(4-F-phenyl) | benzene | |
| 16 | O | H | 4,—O(CH₂)₄O—(3-CF₃-phenyl) | benzene | |
| 17 | S | H | 4,—OCH₂—phenyl | benzene | |
| 18 | O | H | 4,—O(CH₂)₄—phenyl | benzene | |
| 19 | O | H | 4,—O(CH₂)₃OCH₂—phenyl | benzene | |
| 20 | O | H | 4,—O(CH₂)₃CH₃ | benzene | |
| 21 | O | H | 4,—O(CH₂)₅CH₃ | benzene | |

TABLE 1-continued

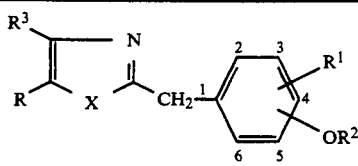

| Compound No. | X | R¹ | OR² | R³ | R⁴ |
|---|---|---|---|---|---|
| 22 | S | H | 4,—O(CH₂)₃CH₃ | | phenyl |
| 23 | O | H | 4,—O—CH₂—CH=C(CH₃)—CH₂CH₂—CH=C(CH₃)CH₃ | | phenyl |
| 24 | O | H | 4,—O—CH₂—CH=C(CH₃)—CH₂CH₂—CH=C(CH₃)—CH₂CH₂—CH=C(CH₃)CH₃ | | phenyl |
| 25 | O | H | 4,—O(CH₂)₄OCH₃ | | phenyl |
| 26 | O | H | 4,—OCH₂C≡CH | | phenyl |
| 27 | O | H | 4,—OCH₂C≡CCH₃ | | phenyl |
| 28 | O | H | 4,—O(CH₂)₃C≡CH | | phenyl |
| 29 | O | H | 4,—O(CH₂)₃C≡C—phenyl | | phenyl |
| 30 | O | 2,—Cl | 4,—O(CH₂)₃C≡C—phenyl | | phenyl |
| 31 | O | H | 4,—OCH₂C≡C(CH₂)₃—C≡C—phenyl | | phenyl |
| 32 | O | H | 4,—O(CH₂)₃C≡CCH₂OH | | phenyl |
| 33 | O | H | 4,—O(CH₂)₃C≡C(CH₂)₃OH | | phenyl |

TABLE 1-continued
[Structure shown at top with R³, N, R, X, CH₂, positions 1-6, R¹, OR² substituents]
| Compound No. | X | R¹ | OR² | R³ | R⁴ |
|---|---|---|---|---|---|
| 34 | O | 2,—Cl | 4,—OCH₂C≡CCH₃ | |  |
| 35 | O | 2,—Cl | 4,—O(CH₂)₃C≡CH | |  |
| 36 | O | H | 4,—OCH₂—(phenyl) | |  |
| 37 | O | H | 4,—OCH₂C≡C(CH₂)₂CH₃ | |  |
| 38 | O | H | 4,—OCH₂C≡CCH₂CH₃ | |  |
| 39 | S | H | 4,—OCH₂C≡CCH₃ | |  |
| 40 | S | H | 4,—O(CH₂)₃C≡CH | |  |
| 41 | O | H | 4,—O(CH₂)₃O—(phenyl)—(CH₂)₂CH₃ | | 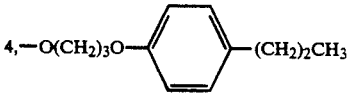 |
| 42 | O | H | 4,—O(CH₂)₃O—(phenyl)—(CH₂)₃CH₃ | |  |
| 43 | O | 3,—Cl | 4,—O(CH₂)₃O—(phenyl) | | 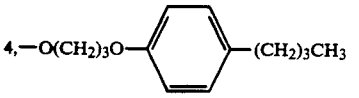 |
| 44 | O | 3,—Cl | 4,—O(CH₂)₄O—(phenyl) | |  |

TABLE 1-continued

| Compound No. | X | R¹ | OR² | R³ | R⁴ |
|---|---|---|---|---|---|
| 45 | O | 3,—Cl | 4,—O(CH₂)₄O—C₆H₅ | C₆H₅ | C₆H₅ |
| 46 | O | 3,—Cl | 4,—O(CH₂)₃OCH₂—C₆H₅ | C₆H₅ | C₆H₅ |
| 47 | O | 3,—Cl | 4,—O(CH₂)₃C≡C—C₆H₅ | C₆H₅ | C₆H₅ |
| 48 | O | 3,—Cl | 4,—OCH₂C≡C(CH₂)₃C≡C—C₆H₅ | C₆H₅ | C₆H₅ |
| 49 | O | 3,—Cl | 4,—OCH₂CH=C(CH₃)CH₂CH₂CH=C(CH₃)₂ | C₆H₅ | C₆H₅ |
| 50 | O | 3,—Cl | 4,—OCH₂CH=CH₂ | C₆H₅ | C₆H₅ |
| 51 | O | 3,—Cl | 4,—O(CH₂)₄OCH₃ | C₆H₅ | C₆H₅ |
| 52 | O | 3,—Cl | 4,—OCH₂C≡CCH₃ | C₆H₅ | C₆H₅ |
| 53 | O | 3,—Cl | 4,—O(CH₂)₃C≡CH | C₆H₅ | C₆H₅ |
| 54 | O | 3,—Cl | 4,—O(CH₂)₃C≡CCH₂OCH₂CH₃ | C₆H₅ | C₆H₅ |
| 55 | O | 3,—Cl | 4,—OCH₂C≡C(CH₂)₃C≡CH | C₆H₅ | C₆H₅ |
| 56 | O | 3,—Cl | 4,—OCH₂C≡C(CH₂)₃C≡CCH₂OCH₂CH₃ | C₆H₅ | C₆H₅ |

TABLE 1-continued

Structure header:
R³ at one position, with N, X, R, CH₂ connected to a benzene ring with positions 1-6, R¹ at position 3, OR² at position 4.

| Compound No. | X | R¹ | OR² | R³ | R⁴ |
|---|---|---|---|---|---|
| 57 | O | 3,—Cl | 4,—O(CH₂)₃C≡C(CH₂)₃C≡CCH₂OH |  | |
| 58 | O | 3,—Cl | 4,—OCH₂C≡C(CH₂)₂CH₃ |  | |
| 59 | O | 3,—Cl | 4,—OCH₂C≡CCH₂CH₃ |  | |
| 60 | O | 3,—Cl | 4,—O(CH₂)₄O— (2-Cl-phenyl) 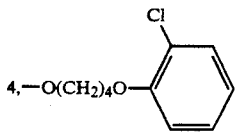 |  | |
| 61 | O | 3,—Cl | 4,—O(CH₂)₄O— (3-Cl-phenyl) 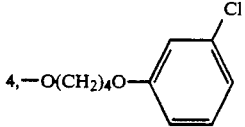 |  | |
| 62 | O | 3,—Cl | 4,—O(CH₂)₄O— (4-Cl-phenyl) 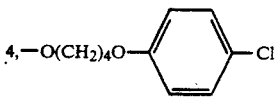 |  | |
| 63 | O | 3,—Cl | 4,—O(CH₂)₄O— (2-CH₃-phenyl) 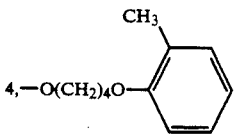 |  | |
| 64 | O | 3,—Cl | 4,—O(CH₂)₄O— (3-CH₃-phenyl) 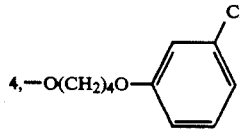 |  | |
| 65 | O | H | 3,—O(CH₂)₃O—phenyl 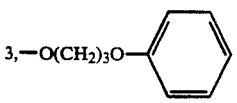 |  | |
| 66 | O | H | 3,—O(CH₂)₄O—phenyl 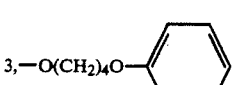 |  | |
| 67 | O | H | 3,—O(CH₂)₃OCH₂—phenyl 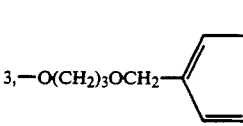 |  | |

TABLE 1-continued

[Structure: R³ and R (on C=C) attached to X, connected to C=N-CH₂-phenyl ring with positions 1-6, R¹ at position 3, OR² at position 4]

| Compound No. | X | R¹ | OR² | R³ | R⁴ |
|---|---|---|---|---|---|
| 68 | O | H | 3,—O(CH₂)₃C≡C—C₆H₅ | | phenyl |
| 69 | O | H | 3,—OCH₂C≡C(CH₂)₃C≡C—C₆H₅ | | phenyl |
| 70 | O | 2,—Cl | 5,—O(CH₂)₄O—C₆H₅ | | phenyl |
| 71 | O | H | 3,—O(CH₂)₃CH₃ | | phenyl |
| 72 | O | H | 3,—OCH₂C≡CH | | phenyl |
| 73 | O | H | 3,—OCH₂C≡CCH₃ | | phenyl |
| 74 | O | H | 3,—O(CH₂)₃C≡CH | | phenyl |
| 75 | O | H | 3,—OCH₂C≡C(CH₂)₃C≡CH | | phenyl |
| 76 | O | H | 3,—O(CH₂)₃≡C(CH₂)₃C≡CCH₂OH | | phenyl |
| 77 | O | 2,—Cl | 5,—OCH₂C≡CCH₃ | | phenyl |
| 78 | O | 2,—Cl | 5,—O(CH₂)₃C≡CH | | phenyl |

TABLE 1-continued
| Compound No. | X | R¹ | OR² | R³ | R⁴ |
|---|---|---|---|---|---|
| 79 | O | 2,—Cl | 5,—O(CH$_2$)$_3$C≡CCH$_2$OCH$_2$CH$_3$ |  | |
| 80 | O | H | 3,—OCH$_2$C≡C(CH$_2$)$_2$CH$_3$ |  | |
| 81 | O | H | 3,—OCH$_2$C≡CCH$_2$CH$_3$ | 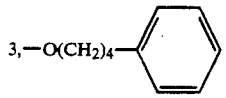 | |
| 82 | O | H | 3,—O(CH$_2$)$_4$—  |  | |
| 83 | S | H | 3,—OCH$_2$C≡CCH$_3$ |  | |
| 84 | S | H | 3,—O(CH$_2$)$_3$C≡CH | 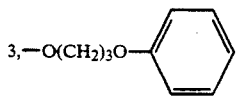 | |
| 85 | S | H | 3,—O(CH$_2$)$_3$O—  | 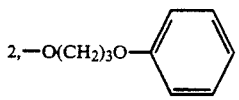 | |
| 86 | O | H | 2,—O(CH$_2$)$_3$O—  | 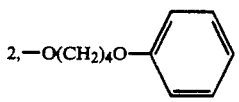 | |
| 87 | O | H | 2,—O(CH$_2$)$_4$O—  | 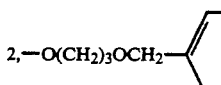 | |
| 88 | O | H | 2,—O(CH$_2$)$_3$OCH$_2$—  | 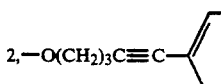 | |
| 89 | O | H | 2,—O(CH$_2$)$_3$C≡C—  | 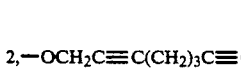 | |
| 90 | O | H | 2,—OCH$_2$C≡C(CH$_2$)$_3$C≡C—  | | |

TABLE 1-continued
| Compound No. | X | R¹ | OR² | R³ | R⁴ |
|---|---|---|---|---|---|
| 91 | O | 2,—Cl | 6,—O(CH$_2$)$_4$O— | |  |
| 92 | O | H | 2,—O(CH$_2$)$_3$CH$_3$ | |  |
| 93 | O | H | 2,—O | |  |
| 94 | O | H | 2,—O | |  |
| 95 | O | H | 2,—OCH$_2$C≡CH | |  |
| 96 | O | H | 2,—OCH$_2$C≡CCH$_3$ | |  |
| 97 | O | H | 2,—O(CH$_2$)$_3$C≡CH | |  |
| 98 | O | H | 2,—OCH$_2$C≡C(CH$_2$)$_3$C≡CH | |  |
| 99 | O | H | 2,—OCH$_2$C≡C(CH$_2$)$_3$C≡CCH$_2$OCH$_2$CH$_3$ | |  |
| 100 | O | 2,—Cl | 6,—OCH$_2$C≡CCH$_3$ | |  |
| 101 | O | H | 2,—O(CH$_2$)$_3$C≡C(CH$_2$)$_3$C≡CCH$_2$OH | |  |

TABLE 1-continued

[Structure: R³ and R (with X) on oxazoline/thiazoline ring connected via N=C–CH₂– to phenyl ring with positions 1–6, R¹ and OR² substituents]

| Compound No. | X | R¹ | OR² | R³ | R⁴ |
|---|---|---|---|---|---|
| 102 | O | H | 2,—OCH₂C≡C(CH₂)₂CH₃ |  | |
| 103 | O | H | 2,—OCH₂C≡CCH₂CH₃ |  | |
| 104 | O | 2,—Cl | 6,—O(CH₂)₃C≡C(CH₂)₃C≡CCH₂OH |  | |
| 105 | O | H | 2,—O(CH₂)₄—[phenyl] | 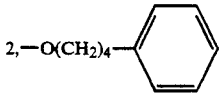 | |
| 106 | S | H | 2,—OCH₂C≡CCH₃ |  | |
| 107 | S | H | 2,—O(CH₂)₃C≡CH |  | |
| 108 | S | H | 2,—O(CH₂)₃O—[phenyl] |  | |
| 109 | O | 3,—Cl | 6,—O(CH₂)₄O—[pyridyl] | 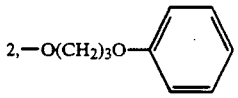 | |
| 110 | O | 3,—Cl | 6,—OCH₂C≡C(CH₂)₃C≡C—[phenyl] |  | |
| 111 | O | 3,—Cl | 6,—OCH₂C≡CCH₃ | 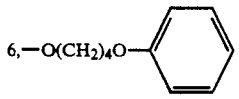 | |
| 112 | O | 3,—Cl | 6,—O(CH₂)₃C≡CH |  | |
| 113 | O | 3,—Cl | 6,—OCH₂C≡C(CH₂)₂CH₃ | 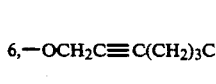 | |

TABLE 1-continued
Structure: R³-C(R)=X-C(=N-CH₂-Ar(R¹)(OR²))-... with aryl positions 1-6, R⁴ on aryl.
| Compound No. | X | R¹ | OR² | R³ | R⁴ |
|---|---|---|---|---|---|
| 114 | O | 3,—Cl | 6,—OCH₂C≡CCH₂CH₃ |  | |
| 115 | O | H | 4,—O(CH₂)₃—O—Ph | 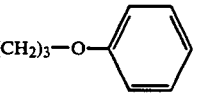 | |
| 116 | O | H | 4,—O(CH₂)₄—O—Ph | 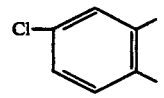 | |
| 117 | O | H | 4,—O(CH₂)₃C≡CH | 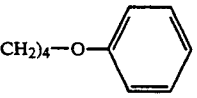 | |
| 118 | O | H | 2,—O(CH₂)₄O—C₆H₄—Cl | 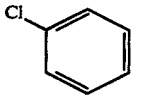 | |
| 119 | O | H | 2,—O(CH₂)₄O—C₆H₃(Cl)₂ | 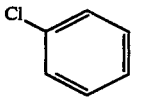 | |
| 120 | O | H | 4,—O(CH₂)₄O—C₆H₃(Cl)₂ | 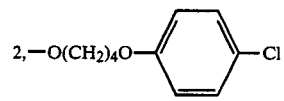 | |
| 121 | O | 3,Cl | 4,—O(CH₂)₄O—C₆H₃(Cl)₂ |  | |
| 122 | O | 3,Cl | 4,—O—(CH₂)₄—O—Ph | 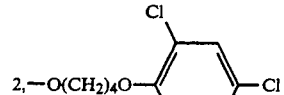 | H |
| 123 | O | 3,Cl | 2,—O—(CH₂)₄O—Ph |  | H |
| 124 | O | 3,Cl | 3,—O(CH₂)₄O—Ph | 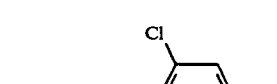 | H |

TABLE 1-continued

| Compound No. | X | R¹ | OR² | R³ | R⁴ |
|---|---|---|---|---|---|
| 125 | O | 3,Cl | 2,—O(CH$_2$)$_3$C≡CH | phenyl | H |
| 126 | O | H | 3,—O(CH$_2$)$_3$C≡CH | phenyl | H |
| 127 | O | H | 4,—O(CH$_2$)$_3$C≡CH | phenyl | H |
| 128 | O | H | 2,—OCH$_2$C≡C—CH$_3$ | phenyl | H |
| 129 | O | H | 3,—OCH$_2$C≡C—CH$_3$ | phenyl | H |
| 130 | O | H | 4,—OCH$_2$C≡C—CH$_3$ | phenyl | H |
| 131 | O | H | 4,—O(CH$_2$)$_4$O—CH$_3$ | phenyl | H |

Then, the process for producing the compound according to the present invention will be explained.

Among the compounds of the present invention represented by the general formula (I), an oxazole derivative or thiazole derivative in which R³ and R⁴ in the formula are not combined together can be synthesized in the following scheme (1) or scheme (2).

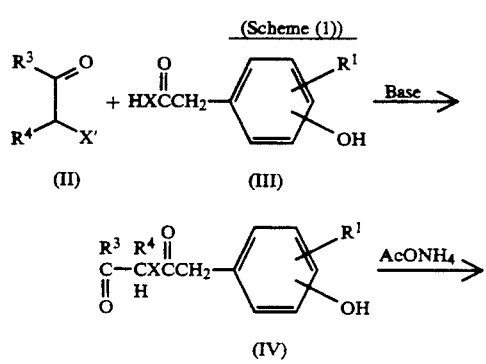

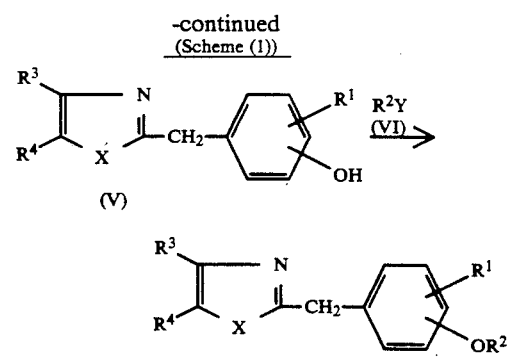

In the above scheme (1), R¹, R², R³, R⁴ and X are as defined above, X' represents a halogen atom and Y represents a halogen atom or a sulfoxy group.

The haloketone (II) and the carboxylic acid (or thiocarboxylic acid)(III) are reacted in a solvent under the presence of a base at 10° to 80° C. for about 1 to 5 days to obtain the compound (IV).

Then the compound (IV) is reacted with ammonium acetate in acetic acid as the solvent at 10° to 120° C. to give a compound (V), and the compound (V) is brought into reaction with the compound (VI) in a solvent under the presence of a base at 10° to 100° C. for about 1 to 24 hours to obtain the compound (I) according to the present invention.

As the base used for the above reaction, there can be mentioned a trialkylamine such as triethylamine, pyridine and lutidine. Further, as the solvent used in the reaction, there can be mentioned, for example, dichloromethane, chloroform, carbon tetrachloride, tetrahydrofuran, dioxane, acetonitrile, benzene, toluene, N,N-dimethylformamide, dimethylsulfoxide and pyridine.

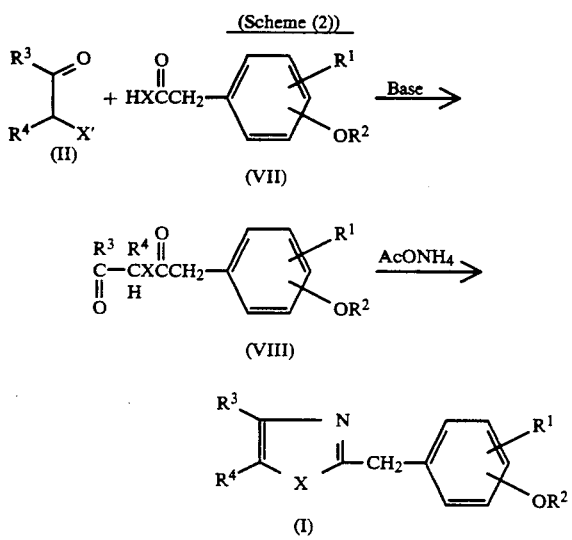

In the scheme (2), $R^1$, $R^2$, $R^3$, $R^4$, X and X' are as defined above.

The haloketone (II) and the carboxylic acid (or thiocarboxylic acid) (VII) are brought into reaction in a solvent under the presence of a base at 10° to 80° C. for about 1-5 days to obtain the compound (VIII).

The base and the solvent used in the reaction are the same as those in the scheme (1) described above.

Then, by reacting the resultant compound (VIII) with ammonium acetate in acetic acid as a solvent at 10° to 120° C., the compound (I) according to the present invention can be obtained.

Among the compounds according to the present invention represented by the formula (I), benzoxazole or benzothiazole derivatives in which $R^3$ and $R^4$ in the formula are combined together form a benzene ring which may have a substituent can be synthesized in accordance with the following scheme (3) or the scheme (4).

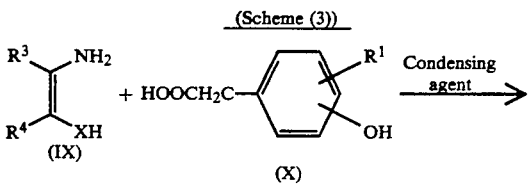

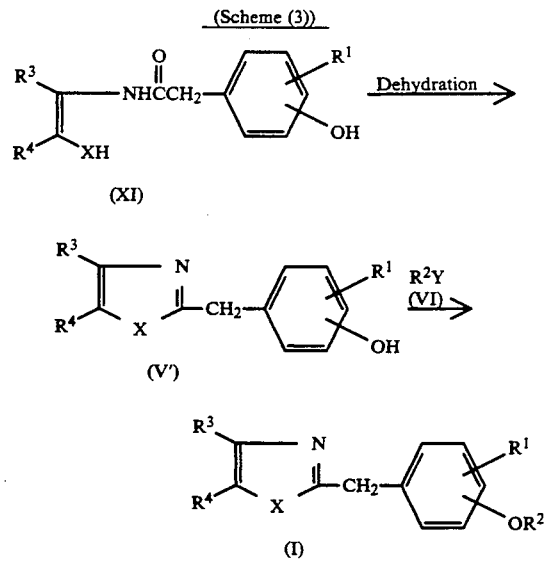

In the scheme (3), $R^1$, $R^2$, $R^3$, $R^4$, X and Y are as defined above.

The amino compound (IX) and the carboxylic acid (X) are brought into reaction under the presence of a condensing agent in a solvent or without solvent at −10° to 230° C. for about 1-24 hours to obtain the amide compound (XI).

Then, the thus obtained amide compound (XI) is reacted, after or without isolation from the reaction system, under the presence of a condensing agent in a solvent or without solvent at −10° to 230° C. for about 1-24 hours to obtain the cyclized compound (V').

As the condensing agent used in the reaction, there can be mentioned dicyclohexylcarbodiimide, ethoxycarbonyl chloride, diphenylphosphoryl azide, 1-ethoxycarbonyl-2-ethoxy-1,2-dihyroquinoline and polyphosphoric acid.

Further, as the solvent used for the reaction, there can be mentioned chloroform, dichloromethane, carbon tetrachloride, tetrahydrofuran, dioxane, benzene, toluene, acetonitrile, N,N-dimethylformamide and dimethylsulfoxide.

The compound (V') can be also obtained by reacting the compound (XI) under the presence of a catalyst in a solvent or without solvent at 100° to 230° C. for 10 min to 24 hours.

As the catalyst usable for the reaction, there can be mentioned hydrogen chloride salt of amine such as pyridine hydrogen chloride and pyrrolidine hydrogen chloride.

Further, as the solvent usable herein, there can be mentioned amines such as pyridine and pyrrolidine, and aprotic polar solvents such as N,N-dimethylformamide and dimethylsulfoxide.

By reacting the compound (V') obtained by the abovementioned reaction with the compound (VI) under the same reaction conditions as those in the scheme (1) mentioned above, the compound (I) according to the present invention can be obtained.

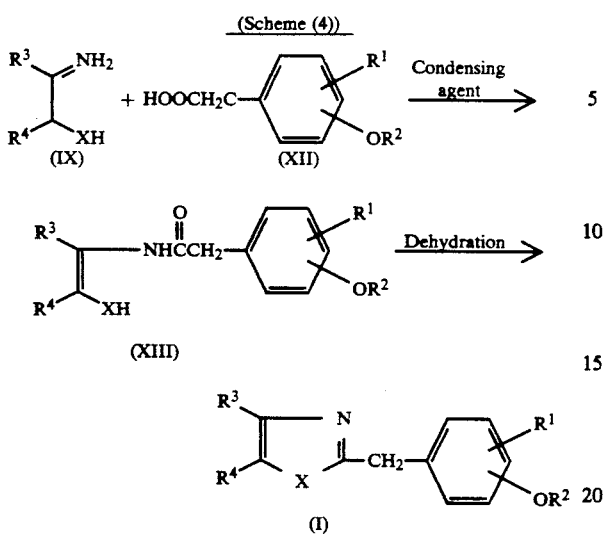

(Scheme (4))

In the scheme (4), $R^1$, $R^2$, $R^3$, $R^4$ and X are as defined above.

The amino compound (IX) and the carboxylic acid (XII) are subjected to condensation under the same reaction conditions as those in the scheme (3) into the compound (XIII), which is then subjected to dehydration reaction under the same reaction conditions as those in the scheme (3) to obtain the compound (I) according to the present invention.

The compound according to the present invention can be isolated and purified in accordance with a usual method, for example, by purification through extraction or column chromatography and, subsequently, by treatment such as crystallization in an appropriate solvent.

As the pharmaceutically acceptable salt for the compound according to the present invention, there can be mentioned salts formed from the compound (I) and an acid such as hydrochloric acid, hydrobromic acid, sulfuric acid, nitric acid, phosphoric acid, methanesulfonic acid, benzenesulfonic acid, acetic acid, citric acid, fumaric acid, maleic acid and succinic acid.

As apparent from test examples described later, since the compound according to the present invention has an inhibition activity to lipoxygenase, it can be used generally for the prevention and treatment of various inflammatory diseases (rheumatis, arthritis, psoriasis, etc.) as well as various allergic diseases (allergic rhinitis, allergic dermatitis, allergic bronchial asthma, etc.).

The compound according to the present invention, when used for therapy, can be formulated into an oral administration from such as tablet and capsule. The compound can be used alone or in combination with a known diluent, flavouring agent, solubilizing agent, lubricant, precipitation inhibitor, binder, tablet-disintegrater, etc. such as magnesium carbonate, magnesium stearate, talc, sucrose, lactose, pectine, dextrine, starch, gelatin, tragachanth, methylcellulose, sodium carboxymethylcellulose, etc.

Also, the compound according to the present invention, when used in the form of a sterilized solution containing other solutes such as sodium chloride or glucose in a sufficient amount to prepare an isotonic solution, can be injected not orally. The compound may be formulated into an aqueous or partially aqueous solution for administration by inhalation or air douche, and, the thus formulated solution may be utilized in an aerosol form.

The compound according to the present invention can also be utilized as ointment or suppository by using a base such as cacao butter, polyethylene glycol, Witepp sol and white petrolatum.

The dosage is dependent on the type of the compositions used, route of administration, condition of disease and patients to be cured, and, preferably selected within the range, usually, from 0.1 to 100 mg/kg as the amount of the effective ingredient.

The present invention will now be described more specifically referring to examples and test examples, but the present invention is not restricted to these examples.

EXAMPLE 1

Synthesis of 2-[4-(3-phenoxy)propoxybenzyl]benzothiazole

Compound No. 1 in Table 1

In 10 ml of N,N-dimethylformamide (DMF), were dissolved 500 mg of 4-(3-phenoxy)propoxyphenyl acetic acid and 220 mg of 2-aminothiophenol, to which 350 mg of triethylamine and 350 mg of diphenylphosphoro azide were added and stirred at a room temperature for 6 hours. The DMF was distilled off under a reduced pressure from the reaction solution and the residue was dissolved into 30 ml of chloroform, then added with an aqueous saturated solution of sodium hydrogen carbonate to carry out the partition followed by collecting the chloroform layer. To the residue obtained by distilling off the chloroform under a reduced pressure from the extract, was added pyridine hydrogen chloride and heated at 220° C. for 30 min. After cooling, purification by silica gel column chromatography and crystallization from petroleum ether, 240 mg of the titled compound having the melting point of 71.5° to 72° C. was obtained.

EXAMPLE 2

Synthesis of 2-[4-(3-phenoxy)propoxybenzyl]benzoxazole

Compound No. 2 in Table 1

In 5 ml of DMF, was added 300 mg of 2-(4-hydroxybenzyl)benzoxazole, to which were added one equivalent of sodium methoxide and then 315 mg of 3-phenoxypropylbromide and stirred at room temperature for 2 hours. The DMF was distilled off under a reduced pressure from the reaction solution and the residue was dissolved into chloroform, washed with an aqueous saturated solution of sodium hydrogen carbonate to collect the chloroform layer. After distilling off the chloroform under a reduced pressure from the extract, the residue was purified by silica gel column chromatography and crystallized from petroleum ether to obtain 172 mg of the titled compound having the melting point of 88° to 89° C.

EXAMPLES 3–121

The compounds Nos. 3–121 in the Table 1 were synthesized by the same procedures as those in Example 2. The melting point of each of the compounds (Compound No. in Table 2 corresponds to the Compound No. in Table 1) is shown in the following Table 2.

TABLE 2

| Compound No. | Melting Point (°C.) |
| --- | --- |
| 3 | 68~69 |
| 4 | oil |
| 5 | 56~57 |
| 6 | 58~59 |
| 7 | oil |
| 8 | 44~44.5 |
| 9 | 48~49.5 |
| 10 | oil |
| 11 | 75~76 |
| 12 | 53.5~54 |
| 13 | 44~45 |
| 14 | 53~54 |
| 15 | 49~51 |
| 16 | 45~47 |
| 17 | 88~90 |
| 18 | 43~45 |
| 19 | 58~59 |
| 20 | oil |
| 21 | oil |
| 22 | oil |
| 23 | oil |
| 24 | oil |
| 25 | oil |
| 26 | 50~51 |
| 27 | 51~52 |
| 28 | 40~41 |
| 29 | 49~51.5 |
| 30 | 75~75.5 |
| 31 | oil |
| 32 | 76~77 |
| 33 | 35~37 |
| 34 | 74~74.5 |
| 35 | 46~46.5 |
| 36 | 41~43 |
| 37 | 42~43 |
| 38 | 47~47.5 |
| 39 | 36~37 |
| 40 | 33~34 |
| 41 | 63~64 |
| 42 | 63~64 |
| 43 | 41~42 |
| 44 | 63~65 |
| 45 | oil |
| 46 | oil |
| 47 | oil |
| 48 | oil |
| 49 | oil |
| 50 | oil |
| 51 | oil |
| 52 | 51~52 |
| 53 | 65~67 |
| 54 | oil |
| 55 | oil |
| 56 | oil |
| 57 | oil |
| 58 | oil |
| 59 | 48.5~49 |
| 60 | oil |
| 61 | 51~52 |
| 62 | 67~68 |
| 63 | oil |
| 64 | 37~37.5 |
| 65 | 62~63 |
| 66 | 65~67 |
| 67 | oil |
| 68 | oil |
| 69 | oil |
| 70 | 65~67 |
| 71 | oil |
| 72 | 58~58.5 |
| 73 | 38~39 |
| 74 | oil |
| 75 | oil |
| 76 | oil |
| 77 | 45~48 |
| 78 | <40 |
| 79 | oil |
| 80 | oil |
| 81 | oil |
| 82 | oil |
| 83 | oil |
| 84 | <30 |
| 85 | 57.5~59 |
| 86 | oil |
| 87 | 66~67 |
| 88 | oil |
| 89 | 68~70 |
| 90 | oil |
| 91 | oil |
| 92 | oil |
| 93 | oil |
| 94 | oil |
| 95 | 46~47 |
| 96 | 52~53 |
| 97 | oil |
| 98 | oil |
| 99 | oil |
| 100 | 101~102 |
| 101 | oil |
| 102 | 32~33 |
| 103 | 53.5~54 |
| 104 | oil |
| 105 | 39~41.5 |
| 106 | 51.5~52.5 |
| 107 | 50 |
| 108 | 56~57 |
| 109 | 56~57 |
| 110 | oil |
| 111 | 70~71.5 |
| 112 | oil |
| 113 | 48~49 |
| 114 | 48~49.5 |
| 115 | 85~87 |
| 116 | 75~76 |
| 117 | 78~79 |
| 118 | 47-48 |
| 119 | 65-66 |
| 120 | 89.5-90.5 |
| 121 | 82-84 |

EXAMPLE 122

Synthesis of
2-[4-(4-phenoxybutyloxy)benzyl]-4-phenyloxazole

Compound No. 122 in Table 1

In 50 ml of dichloromethane, were dissolved 6.09 g of 4-hydroxyphenyl acetic acid and 7.96 g of phenacyl bromide were dissolved, to which 5.6 ml of triethylamine was added and stirred at room temperature for 2 days. After washing the reaction solution with a 10% hydrochloric acid, it was further washed with an aqueous saturated solution of sodium hydrogen carbonate. After distilling off the dichloromethane under a reduced pressure from the solution, the residue was dissolved in 80 ml of acetic acid and refluxed for three hours with addition of 12.3 g of ammonium acetate. The acetic acid was distilled off under a reduced pressure from the solution. The residue was dissolved in dichloromethane, washed with a 10% hydrochloric acid and an aqueous saturated solution of sodium hydrogen carbonate, and then, the dichloromethane layer was collected. After drying the liquid extract over magnesium sulfate, it was concentrated under a reduced pressure, adsorbed on silica gel column, eluted with chloroform and then crystallized from isopropyl ether to obtain 3.65 g of 2-(4-hydroxybenzyl)-4-phenyloxazole having the melting point of 122° to 124° C.

In 5 ml of DMF, was dissolved 300 mg of 2-(4-hydroxybenzyl)-4-phenyloxazole obtained above. One equivalent of sodium methoxide was added to the solution and then 365 mg of 4-phenoxybutyl bromide was added and stirred at room temperature for 16 hours. After distilling off the DMF under a reduced pressure from the reaction solution, the residue was dissolved in chloroform, washed with an aqueous saturated solution of sodium hydrogen carbonate and the chloroform layer was collected. The liquid extract was concentrated under a reduced pressure, adsorbed on a silica gel column, eluted with dichloromethane and, thereafter, the aimed fraction was collected and the solvent was distilled off to obtain 351 mg of the titled compound having the melting point of 113° to 114° C.

EXAMPLES 123–131

Compounds Nos. 123–131 shown in Table 1 were synthesized in the same procedures an in Example 122.

The melting point for each of the compounds is shown in the following Table 3 (Compound numbers in Table 3 correspond to the Compound numbers in Table 1).

TABLE 3

| Compound No. | Melting Point (°C.) |
| --- | --- |
| 123 | 50~51 |
| 124 | 72~73 |
| 125 | 60~60.5 |
| 126 | 42~43.5 |
| 127 | 52~53 |
| 128 | 50~51 |
| 129 | 64.5~65.5 |
| 130 | oil |
| 131 | 32~33 |

TEST EXAMPLE 1

Measurement of the Inhibition Activity to Lipoxygenase

In 0.9 ml of Hunks' solution, were suspended $2 \times 10^6$ of abdominal cells of Wister rat (7 to 12 week-age) and incubated at 37° C. for 15 min after adding $10^{-7}M$ of arachidonic acid and the compound of the present invention dissolved in ethanol, or only $10^{-7}M$ of arachidonic acid and ethanol as a control. Further, 100 μl of 5 μg/μl of calcium inonophore A-23187 was added and the incubation was further continued at 37° C. for 15 min to produce leukotrienes. After cooling the reaction mixture with ice for 20 min to terminate the reaction, the reaction mixture was subjected to centrifugation at 4° C. for 10 min at 3000 rpm. The inhibition activity to lipoxygenase of the compound according to the present invention was measured by bioassay of leukotrienes contained in the resultant supernatants by using a Magunus' device while taking the contraction reaction of ileum extirpated from guinea pig as the indication. The inhibition rate of the compound according to the present invention was calculated based on the ratio of the suppression due to the compound with respect to the extent of the contraction reaction in the control group, and the intensity of inhibition based thereon is shown in the following Tables 4 and 5 (Compound numbers in Tables 4 and 5 correspond to the Compound numbers in Table 1). Table 4 shows the results when the compound according to the present invention was used in an amount of $10^{-5}M$ (final concentration) and Table 5 shows the result when used in an amount of $10^{-6}M$ (final concentration). Further, Nordihydroguaiaretic acid (NDGA) known to have an effect of suppressing the formation of leukotrienes from arachidonic acid was used as a control.

TABLE 4

| Compound No. | Inhibition intensity |
| --- | --- |
| 1 | +++ |
| 2 | +++ |
| 5 | +++ |
| 6 | +++ |
| 7 | ++ |
| 10 | ++ |
| 15 | ++ |
| 19 | +++ |
| 25 | ++ |
| 29 | +++ |
| 34 | ++ |
| 37 | +++ |
| 44 | +++ |
| 47 | +++ |
| 51 | +++ |
| 53 | +++ |
| 55 | ++ |
| 57 | +++ |
| 62 | ++ |
| 71 | +++ |
| 73 | +++ |
| 89 | ++ |
| 90 | +++ |
| 96 | +++ |
| 98 | ++ |
| 100 | +++ |
| 109 | ++ |
| 112 | ++ |
| 129 | ++ |
| NDGA | ± |

Inhibition intensity
± Inhibition rate 0 to 20%
+ Inhibition rate 20 to 50%
++ Inhibition rate 50 to 80%
+++ Inhibition rate 80 to 100%

TABLE 5

| Compound No. | Inhibition intensity |
| --- | --- |
| 1 | + |
| 2 | + |
| 5 | + |
| 7 | + |
| 10 | + |
| 15 | + |
| 19 | ++ |
| 25 | + |
| 29 | + |
| 37 | + |
| 44 | ++ |
| 47 | |
| 51 | ++ |
| 53 | ++ |
| 62 | + |
| 73 | + |
| 89 | + |
| 90 | + |
| 100 | ++ |
| 112 | + |

Inhibition intensity + Inhibition rate 20 to 50%
Inhibition intensity ++ Inhibition rate 50 to 80%

TEST EXAMPLE 2

Measurement of the Suppressing Effect on Ear Edema Caused by Arachidonic Acid

The thickness of auricles of ICR male mice of 6 week-age was measured by using a micrometer. On both sides of one of the auricles of each mouse, was applied 2 mg of arachidonic acid dissolved in acetone as the inflammatory agent to cause inflammation thereon. The thickness of the auricle after one hour of the application was measured and the difference between the thickness obtained and the thickness before the application was taken as the value of ear edema. The compound according to the present invention dissolved in ethanol or only ethanol as a control were orally administrated or applied localy. In the case of oral administration, 50 mg/kg of the compound according to the present invention was administrated one hour before the application of the inflammatory agent, and 0.1 mg/auricle was applied 30 min before the application in the case of local application.

The suppression rate of ear edema of the compound according to the present invention was calculated based on the ratio of the suppression to the value of ear edema in the control group and the results are shown in Tables 6 and 7 (Compound numbers in Tables 6 and 7 correspond to the Compound numbers in Table 1).

Table 6 shows the suppression rate by oral administration and Table 7 shows the suppression rate by local application. Further, benoxaprofen and NDGA were used as the comparison.

TABLE 6

| Compound No. | Suppression rate (%) |
|---|---|
| 44 | 80.7 |
| 53 | 85.1 |
| 71 | 77.9 |
| 73 | 85.1 |
| 96 | 71.8 |
| Benoxaprofen | 15.3 |

TABLE 7

| Compound No. | Suppression rate (%) |
|---|---|
| 6 | 48.5 |
| 34 | 42.9 |
| 37 | 42.1 |
| 55 | 45.6 |
| 57 | 49.8 |
| 62 | 32.9 |
| 98 | 50.2 |
| 109 | 48.5 |
| 125 | 41.7 |
| NDGA | 18.2 |

From the Test Examples 1 and 2, it is apparent that the compound according to the present invention has an effect of inhibiting lipoxygenase and also has a suppression effect for edema caused by arachidonic acid.

TEST EXAMPLE 3

Acute Toxicity to Mouse

The compounds according to the present invention (Compound No. 44 in Table 1) suspended in an aqueous 1% tragacanth solution was orally administrated by 2000 mg/kg to 6 week-age ICR male mice. Condition and body weight were observed over seven days after the administration, but no change was recognized at all. After the completion of the observation, an anatomic inspection was carried out, but no abnormality was observed.

What is claimed is:

1. A heterocyclic compound represented by the following formula (I):

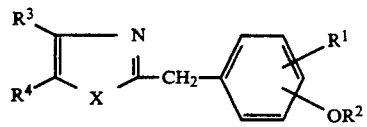

wherein X represents an oxygen atom; $R^1$ represents a hydrogen atom or a halogen atom; $R^2$ represents a $C_2$-$C_{10}$ alkoxyalkyl group, $C_3$-$C_{15}$ alkenyl group, $C_7$-$C_{12}$ aralkyl group, $C_8$-$C_{18}$ aralkyloxyalkyl group, $C_7$-$C_{12}$ aryloxyalkyl group, $C_3$-$C_{10}$ alkynyl group, $C_4$-$C_{12}$ alkadienyl group, $C_6$-$C_{18}$ alkatrienyl group, $C_6$-$C_{12}$ alkadiynyl group, or $C_6$-$C_{12}$ alkatriynyl group, wherein said aryloxyalkyl group, alkynyl group, alkadienyl group, alkatrienyl group, alkadiynyl group and alkatriynyl group is unsubstituted or has at least one substituent selected from the group consisting of halogen atoms, $C_1$-$C_4$ alkyl group, $C_1$-$C_4$ halogenated alkyl group, phenyl group, hydroxyl group and $C_1$-$C_4$ alkoxy group; and each of $R^3$ and $R^4$ independently represents a hydrogen atom, $C_1$-$C_6$ alkyl group, phenyl group or tolyl group, or $R^3$ and $R^4$ may be combined together to form a benzene ring which may have at least one halogen atom; or a pharmaceutically acceptable salt thereof.

2. A heterocyclic compound or a pharmaceutically acceptable salt thereof according to claim 1, wherein $R^2$ is a $C_2$-$C_6$ alkoxyalkyl group, $C_3$-$C_{10}$ alkenyl group, $C_7$-$C_{12}$ aralkyl group, $C_8$-$C_{12}$ aralkyloxyalkyl group, $C_7$-$C_{12}$ aryloxyalkyl group which may have at least one substituent selected from the group consisting of halogen atoms, $C_1$-$C_4$ alkyl group and $C_1$-$C_4$ halogenated alkyl group, $C_3$-$C_{10}$ alkynyl group which may have at least one substituent selected from the group consisting of phenyl groups, hydroxyl group and $C_1$-$C_4$ alkoxyl group, $C_5$-$C_{12}$ alkyldienyl group, $C_7$-$C_{18}$ alkyltrienyl group, or $C_6$-$C_{12}$ alkyldiynyl group which may have at least one substituent selected from the group consisting of phenyl group, hydroxyl group and $C_1$-$C_4$ alkoxy group; and each of $R^3$ and $R^4$ independently represents a hydrogen atom or phenyl group, or $R^3$ and $R^4$ may be combined together to form a benzene ring which may have at least one halogen atom.

3. A heterocyclic compound or a pharmaceutically acceptable salt thereof according to claim 2, wherein $R^2$ is a $C_2$-$C_6$ alkoxyalkyl group, $C_3$-$C_{10}$ alkenyl group, $C_7$-$C_{10}$ aralkyl group, $C_8$-$C_{10}$ aralkyloxyalkyl group, $C_9$-$C_{12}$ aryloxyalkyl group which may have at least one substituent selected from the group consisting of chlorine atom, fluorine atom, $C_1$-$C_4$ alkyl group and trifluoromethyl group, $C_3$-$C_8$ alkynyl group which may have at least one substituent selected from the group consisting of phenyl group, hydroxyl group and $C_1$-$C_4$ alkoxy group, $C_5$-$C_{10}$ alkyldienyl group, $C_7$-$C_{15}$ alkyltrienyl group, or $C_8$-$C_{11}$ alkyldiynyl group which may have at least one substituent selected from the group consisting of phenyl group, hydroxyl group and $C_1$-$C_4$ alkoxy group; and each of $R^3$ and $R^4$ independently represents a hydrogen atom or phenyl group, or $R^3$ and $R^4$ may be combined together to form a benzene ring which may have at least one chlorine atom.

4. A heterocyclic compound or a pharmaceutically acceptable salt thereof according to claim 3, wherein $R^2$ is a $C_2$-$C_6$ alkoxyalkyl group, $C_8$-$C_{10}$ aralkyloxyalkyl group, $C_9$-$C_{12}$ aryloxyalkyl group which may have at least one substituent selected from the group consisting of chlorine atom, fluorine atom, $C_1$-$C_4$ alkyl group and trifluoromethyl group, $C_3$-$C_8$ alkynyl group which may have at least one substituent selected from the group consisting of phenyl group, hydroxyl group and $C_1$-$C_4$ alkoxy group, or $C_8$-$C_{11}$ alkyldiynyl group which may have at least one substituent selected from the group consisting of phenyl group, hydroxyl group and $C_1$-$C_4$ alkoxy group; and each of $R^3$ and $R^4$ independently represents a hydrogen atom or phenyl group, or $R^3$ and $R^4$ may be combined together to form a benzene ring which may have at least one chlorine atom.

5. A heterocyclic compound or a pharmaceutically acceptable salt thereof according to claim 4, wherein $R^1$ is a hydrogen atom or chlorine atom.

6. A heterocyclic compound or a pharmaceutically acceptable salt thereof according to claim 5, wherein $R^3$ and $R^4$ are combined together to form a benzene ring which may have at least one chlorine atom.

7. A pharmaceutical composition which comprises a pharmaceutically effective amount of the heterocyclic compound or the pharmaceutically acceptable salt thereof according to any one of claims 1 to 6 and a pharmaceutically acceptable adjuvant.

8. A pharmaceutical composition according to claim 7, which is effective as an anti-inflammatory agent when the dosage of the effective ingredient is within the range of 0.1 to 100 mg/kg.

9. A pharmaceutical composition according to claim 7, which is effective as an anti-allergic agent when the dosage of the effective ingredient is within the range of 0.1 to 100 mg/kg.

* * * * *